US008628690B2

(12) United States Patent
Mora-Gutierrez et al.

(10) Patent No.: US 8,628,690 B2
(45) Date of Patent: *Jan. 14, 2014

(54) NANOEMULSION COMPOSITIONS AND METHODS OF USE THEREOF

(75) Inventors: Adela Mora-Gutierrez, Houston, TX (US); Michael H Gurin, Glenview, IL (US)

(73) Assignee: The Texas A&M University System, College Station, TX (US)

( * ) Notice: Subject to any disclaimer, the term of this patent is extended or adjusted under 35 U.S.C. 154(b) by 202 days.

This patent is subject to a terminal disclaimer.

(21) Appl. No.: 11/306,582

(22) Filed: Jan. 3, 2006

(65) Prior Publication Data

US 2007/0085058 A1   Apr. 19, 2007

Related U.S. Application Data

(63) Continuation-in-part of application No. 10/784,842, filed on Feb. 23, 2004, now Pat. No. 7,118,688.

(60) Provisional application No. 60/593,280, filed on Jan. 4, 2005.

(51) Int. Cl.
| C09K 15/32 | (2006.01) |
| C09K 15/22 | (2006.01) |
| C09K 15/20 | (2006.01) |
| A23J 7/00  | (2006.01) |
| C07F 9/02  | (2006.01) |

(52) U.S. Cl.
USPC ............. 252/400.21; 252/400.22; 252/401; 252/402; 426/602; 426/604; 426/631; 426/662; 435/68.1; 435/272

(58) Field of Classification Search
USPC ........ 252/400.21, 400.22, 401, 402; 424/405, 424/486, 401, 94.1, 491; 426/99, 602, 604, 426/631, 662; 428/402.21; 514/12; 435/68.1, 272
See application file for complete search history.

(56) References Cited

U.S. PATENT DOCUMENTS

| 4,898,780 | A |   | 2/1990  | Seitz |  |
| 4,963,385 | A | * | 10/1990 | Antrim et al. | 426/602 |
| 5,104,674 | A | * | 4/1992  | Chen et al. | 426/573 |
| 5,405,766 | A |   | 4/1995  | Kallury et al. |  |
| 5,552,167 | A |   | 9/1996  | Taylor et al. |  |
| 5,609,749 | A |   | 3/1997  | Yamauchi et al. |  |
| 5,650,190 | A | * | 7/1997  | Buikstra et al. | 426/602 |
| 5,834,427 | A | * | 11/1998 | Han et al. | 514/12 |
| 6,140,375 | A | * | 10/2000 | Nagahama et al. | 516/73 |
| 6,916,490 | B1 |  | 7/2005  | Garver et al. |  |
| 7,393,548 | B2 | * | 7/2008 | Friedman | 424/725 |
| 2002/0188024 | A1 | * | 12/2002 | Chilton et al. | 514/560 |
| 2003/0059474 | A1 |   | 3/2003  | Scott et al. |  |
| 2003/0228339 | A1 |   | 12/2003 | El-Nokaly et al. |  |
| 2004/0005700 | A1 |   | 1/2004  | Surber et al. |  |
| 2004/0043013 | A1 |   | 3/2004  | McCleary |  |
| 2004/0097472 | A1 |   | 5/2004  | West et al. | 424/400 |
| 2004/0151750 | A1 |   | 8/2004  | O'Leary et al. |  |
| 2004/0247683 | A1 |   | 12/2004 | Popescu et al. |  |
| 2005/0003386 | A1 |   | 1/2005  | Bazan et al. |  |
| 2005/0048088 | A1 | * | 3/2005  | Zulli et al. | 424/401 |
| 2005/0163727 | A1 |   | 7/2005  | Doyle et al. |  |
| 2005/0184275 | A1 |   | 8/2005  | Mora-Gutierrez et al. |  |
| 2005/0211572 | A1 |   | 9/2005  | Buck et al. |  |
| 2005/0238790 | A1 | * | 10/2005 | Ishimoto et al. | 426/656 |

FOREIGN PATENT DOCUMENTS

| GB | 2160098    | 12/1985 | ............... A61K 8/64 |
| WO | WO 92/11844 | 7/1992  | ............... A61K 47/48 |
| WO | WO 96/29893 | 3/1996  | ............... A23L 1/015 |

OTHER PUBLICATIONS

A. Mora-Gutierrez, T. F. Kumosinski and H. Y. Farrell, Jr, Quantification of $\alpha s1$-case in goat milk from French Alpine and anglo-nubian breeds using reversed-phase high performance liquid chromatography, J. Dairy Sci. 74, 3303-3307, 1991.*

Cavamax CoQ10, The highly bioavailble coenzyme Q10 powder, http://www.wacker.com/cms/media/publications/downloads/6201_EN.pdf.*

* cited by examiner

*Primary Examiner* — Bijan Ahvazi
(74) *Attorney, Agent, or Firm* — J. Peters Paredes; Rosenbaum IP

(57) ABSTRACT

A nanoemulsion composition having enhanced oxidative stability, emulsion stability, and health benefits. The composition may include individual ingredients or a synergistic blend of non-reducing sugars, sugar polyols, medium-chain triglycerides, polysaccharides, polyphenols, phospholipids, chitosan, and alpha-casein, beta-casein, kappa-casein or protein fragments, glycopeptides, phosphopeptides. The composition may optionally be further utilized for the prevention of hypercholesterolemia or bone (and teeth) mineral loss.

32 Claims, No Drawings

NANOEMULSION COMPOSITIONS AND METHODS OF USE THEREOF

CROSS-REFERENCE OF RELATED APPLICATIONS

This application claims priority from U.S. Provisional Patent Application Ser. No. 60/593,280 filed Jan. 4, 2005 and titled "Nanoemulsion Compositions and Methods of Use" and is a continuation in part of U.S. patent application Ser. No. 10/784,842 titled "Antioxidant Compositions and Methods of Use", recently filed on the 23rd of Feb. 2004 which is hereby incorporated by reference with priority claims.

FIELD OF THE INVENTION

The present invention relates to nanoemulsion compositions, particularly compositions formed from natural ingredients, and methods for using said compositions to enhance efficacy and bioavailability of actives. The invention comprised of a polycationic complexation system further provides enhanced bioavailability of calcium and phospholipids for applications ranging from oral care to memory enhancers.

BACKGROUND

It is known that whatever their kind and origin, nutraceuticals and pharmaceuticals, that are not readily water soluble, have relatively limited bioavailability. Many factors are recognized in the art as limiting bioavailability including relatively limited membrane fluidity, solubility, unstable dispersions or emulsions. Additionally the presence of competing non-actives for the same enzymatic functionality, such as Omega-6 versus Omega-3. Mammals cannot interconvert the omega-3 and omega-6 fatty acids and their metabolism requires the same desaturation enzymes.

Their presence in food is of great importance since they cannot be synthesized by human and animal tissues and should thereby be provided with the diet. In tissues these essential fatty acids are converted to longer and more unsaturated fatty acids of the Omega-6 and Omega-3 families, such as arachidonic acid (AA), eicosapentaenoic (EPA), and docosahexaenoic (DHA), which are present in marine oils (fish, microalgae) in relatively high amounts. The health benefits of linoleic acid, alpha-linolenic acid, AA, EPA and DHA are well documented in the literature. These benefits include hypolipidemic, anti-thrombotic, and anti-inflammatory properties. They are also essential fats for growth, brain function, and visual acuity, especially for infants. Omega-3's are further recognized for their positive impact on psychiatric, brain, and neurologic conditions.

Many products ranging from functional foods and confectioneries to nutraceuticals and pharmaceuticals are emulsions or may be made into emulsions. An emulsion is a colloidal dispersion of two immiscible liquids, such as oil and water, in the form of droplets. If oil droplets are finely dispersed in water, then this is an oil-in-water or "O/W" emulsion. When water droplets are finely dispersed in oil, then this is a water-in-oil or "W/O" emulsion. O/W and W/O emulsions play a prominent role in the preparation of a wide range of products including foods, pharmaceutical products and cosmetics. It would be thus desirable to provide enhanced bioavailability compositions formed from natural ingredients and methods to effectively increase efficacy within highly polyunsaturated oils in O/W and W/O emulsions.

SUMMARY OF THE INVENTION

The present invention relates to compositions and methods for enhancing the bioavailability within highly polyunsaturated lipids in O/W and W/O nanoemulsions. Particular embodiments of the present invention relate to a process for the delivery of actives within O/W and W/O nanoemulsions containing highly polyunsaturated lipids, characterized in that effective quantities of tocopherols, beta-carotene, egg yolk or soybean phospholipids, and sucrose or sorbitol are incorporated in the O/W and W/O nanoemulsions by high-pressure homogenization.

When used in the presence of caprine caseinophosphopeptide, eggplant (LBJ 10), and citric acid, certain embodiments of the present invention show long-term emulsion stability, very high surface area, and micelles within the range of 5-30 nanometers. In addition, the nanoemulsion compositions may offer nutritional and pharmacological benefits including: (1) enhanced membrane fluidity, having improved brain functions (e.g., memory, reduced ADD and ADHD, etc.) activity in animal bodies; (2) enhanced soluble complexes with calcium and chitosan for bioadhesion, providing remineralization of teeth and bone in animal bodies, (3) enhanced delivery of actives including the families of recognized fat-soluble antioxidants (tocopherols, tocotrienols, beta-carotene, Coenzyme $Q_{10}$), choline, carnitine, and essential fatty acids (DHA, EPA).

Specific embodiments of the present invention are further described in the following detailed description.

DETAILED DESCRIPTION

The term electron transfer mediator, which is interchangeably used with electron transport mediator, is defined as means of increasing the effective mobilization of electrons including the tunneling or bridging across molecular scale interfaces. Without being bound by theory, an electron transfer mediator provides a low resistance path for electron mobility.

The term "alkalide" is defined as a class of ionic compounds where the cations are of the Type I group (Alkali) elements Na, K, Rb, Cs (no known 'Lithide' exists). The cation is a alkali cation complexed by a large organic complexant. The resulting chemical form is A+[Complexant] B−, where the complexant is either a Cryptand, Crown Ether, or Aza-Crown.

The term "electride" is defined as being just like alkalides except that the anion is presumed to be simply an electron which is localized to a region of the crystal between the complexed cations.

The term ubiquinone 50, 2,3-dimethoxy-5-methyl6-pentacontdacaenyl-benzoquinone is also hereinafter referred to as coenzyme $Q_{10}$ or CoQ10.

The present invention includes compositions and methods for enhancing bioavailability and efficacy. The nanoemulsion compositions may enhance delivery of highly polyunsaturated lipids. They may include non-reducing sugars, sugar polyols, medium-chain triglycerides, sulfated polysaccharides, caseinophosphopeptides, phospholipids, chitosan and polyphenols. These nanoemulsion compositions may be used in O/W or W/O emulsions or further subjected to post processing to yield free flowing powders as recognized in the art (e.g., spray drying, freeze drying, absorption plating, etc.).

Selected embodiments contain sulfated polysaccharides. These may include compounds containing at least one polymeric sugar moiety covalently attached to a sulfate group. One example of a sulfated polysaccharide is the carrageenan class of compounds. Other examples of sulfated polysaccharides include chondroitin sulfate, sulfated cyclodextrins, dextran sulfate and heparin sulfate.

The nanoemulsion compositions may also include ingredients selected from the group of non-reducing sugars, sugar polyols, medium-chain triglycerides, polysaccharides, alpha-casein, beta-casein, kappa-casein or protein fragments, glycopeptides, phosphopeptides, alpha, beta, gamma or delta tocopherols, alpha, beta, gamma or delta tocotrienols, tocopherols, tocotrienols, beta-carotene, phospholipids and chitosan, or combinations thereof.

The nanoemulsion compositions may also include pH modifiers including citric acid, ascorbic acid, gluconic acid, and chelating agents including citric acid, choline citrate or combinations thereof.

The nanoemulsion compositions may include polyphenols, including polyphenols derived from the fruit of *Solanum melongena*.

In selected embodiments, the nanoemulsion compositions may include food, beverage, and confectionery ingredients including: non-reducing sugars, sugar polyols, or combinations thereof; modified starches; polysaccharides; glycerides selected from enzymatically modified oils, fats, and fatty acids of mono-, di-, and tri-glycerides; glycerides selected from lipolyzed modified oils, fats, and fatty acids of mono-, di-, and tri-glycerides; fruit concentrate sweetener as humectant that comprises a blend of hydrolyzed starch having a dextrose equivalent (D.E.) of up to approximately 25; fruit juice or fruit syrup concentrate of at least approximately 40% soluble solids and approximately 0% insoluble solids thereby forming a liquor having a dry weight composition of approximately 40 to approximately 65% complex carbohydrates; and approximately 35 to approximately 55% simple sugars from the fruit juice or fruit syrup concentrate; and approximately 0 to approximately 5% nutritional components occurring naturally in the fruit juice or fruit syrup concentrate; cocoa powder; Sucralose; and combinations thereof.

In other embodiments, the nanoemulsion compositions may be made into products including: hypercholesterolemia prevention products in a mammal comprised of calcium and magnesium salts; bone mineral loss prevention products in a mammal comprised of calcium and magnesium salts; oils rich in Omega-3 products comprised of calcium and magnesium salts; oil-soluble flavor products; oil-soluble vitamin, nutraceutical, or pharmaceutical products; products having vegetable oils including rice bran oil, flax, chia, hemp, castor, soybean, lesquerella, dehydrated castor oil, rich in Omega-3, or conjugated linoleic acid, animal oils including fish, egg, poultry, and beef oils rich in Omega-3, or conjugated linoleic acid, or combinations thereof; microalgae oils rich in Omega-3, or conjugated linoleic acid, or combinations thereof; beverage products being transparent comprised of calcium and magnesium salts; cocoa products having improved creaminess, reduced bitterness, and reduced oxidation; protein rich products, comprised of high-methoxyl pectins or pectin alginates or combinations thereof having reduced protein settling and sedimentation; protein rich products having reduced protein settling and sedimentation; oil-in-water micro- and nano-emulsions having increased emulsion and oxidation stability; or water-in-oil micro- and nano-emulsions having increased emulsion and oxidation stability.

The term "Omega-3" includes all enzymatically altered forms of Alpha-linolenic including Stearidonic acid, Eicosapentaenoic acid "EPA", and Docosahexaenoic acid "DHA".

The term "oil rich in Omega-3" includes all oils having greater than 20% Omega-3 content.

The present invention may function as an antioxidant in a variety of ways. For instance, sucrose has demonstrated its potential as a fat-solubilizing agent for natural vitamins such as provitamin A (beta-carotene) and vitamin E (tocopherol) as well as polyphenolic compounds and caprine caseinophosphopeptide and as an antioxidant agent (invert sugar) in fat emulsions.

The nanoemulsion compositions may also include polysaccharides such as sulfated polysaccharides. Sulfated polysaccharides may include iota-, kappa-, or lambda-carrageenan, or combinations thereof.

Compositions of the present invention may also include alpha-casein, beta-casein, kappa-casein or protein fragments, glycopeptides, phosphopeptides and combinations thereof. Phosphopeptides may include phosphopeptides high in alpha.sub.s2.-casein and medium-chain triglycerides such as caseinophosphopeptides. Caseinophosphopeptides may be isolated from caprine (goat) milk to produce caprine caseinophosphopeptide. Caseinophosphopeptides have a particularly potent ability to form soluble complexes with calcium. The increased solubility of the calcium complex may further enhance the mineral absorption to remineralize teeth, especially through the chitosan adhesion within the oral cavity.

Nanoemulsion compositions may further include alpha, beta, gamma or delta tocopherols, alpha, beta, gamma or delta tocotrienols, tocopherols, tocotrienols, beta-carotene, phospholipids, chitosan or combinations thereof. A preferred mix of tocotrienols and tocopherols is extracted from palm sources.

The nanoemulsion compositions may also include polyphenols. A preferred polyphenol is derived from the fruit of *Solanum melongena*. Additional preferred polyphenols are derived from apple, cocoa, grapes, pomegranate, and tea.

Fat emulsion particles containing sucrose or sorbitol increase the solubility (and therefore, dispersion) of tocopherol (vitamin E) and beta-carotene (provitamin A) present in flaxseed oil. Fat particles containing sucrose or sorbitol will also increase the solubility (dispersion) of cocoa (polyphenolic compounds), eggplant-carrageenan complex (polyphenolic compounds) and caprine caseinophosphopeptide-chitosan complex. The enhanced antioxidant activity observed in O/W emulsions containing Canadian flaxseed oil stems from the cooperation among tocopherols, beta-carotene, phospholipids, sorbitol, proprietary cocoa mix, and selected antioxidant compositions of the present invention. The chitosan further enhances bioadhesion, which for oral consumption of actives further improves the efficacy of the active by encouraging sublingual and buccal administration thus avoiding gastrointestinal deterioration.

Phospholipids used in embodiments of the invention may include phospholipids from the group of egg yolk, soybean phospholipids, or combinations thereof. TBA studies confirm the synergistic antioxidant effects among soybean phospholipids (lecithin), beta-carotene (provitamin A), tocopherol (vitamin E), and sorbitol (sugar alcohol) or sucrose (non-reducing sugar) in flaxseed oil-based nanoemulsions. The resulting flaxseed oil-based nanoemulsions and the further use of soybean phospholipids, sorbitol or sucrose along with homogenization minimize the lipid oxidation of Omega-3, Omega-6, and Omega-9 fatty acids. The shelf life of these essential polyunsaturated fatty acids (Omega-3, Omega-6, Omega-9) in O/W nanoemulsions are therefore greatly extended by some antioxidant compositions of the present invention. Identical benefits are realized with a proprietary cocoa mix and subsequent high-pressure homogenization.

Lecithin is widely used in lipid-based food products as an antioxidant synergist. The structure of phospholipid molecules enables lecithin to establish a protective coating on the surface of the oil droplet, thereby retarding lipid oxidation. The process of homogenization entraps not only the phospholipid molecules but also the tocopherol and beta-carotene molecules in the oil droplets that result in enhanced protection against lipid oxidation. The production of low-fat products is further improved by the method of incorporating selected antioxidant compositions of the invention and egg yolk phospholipids to impart a rich and creamy mouthfeel characteristic in low-fat products. Lecithin also has importance in increasing efficacy due to the choline present.

Phosphatidylcholine is a phospholipid that is a major constituent of cell membranes. Choline comprises about 15% of the weight of phosphatidylcholine. Phosphatidylcholine is also known as PtdCho and lecithin. Lecithins containing phosphatidylcholine are produced from vegetable, animal and microbial sources, but mainly from vegetable sources. Soybean, sunflower and rapeseed are the major plant sources of commercial lecithin. Soybean is the most common source. Eggs themselves naturally contain from 68 to 72% phosphatidylcholine, while soya contains from 20 to 22% phosphatidylcholine. Phosphatidylcholine is important for normal cellular membrane composition and repair. Phosphatidylcholine is also the major delivery form of the essential nutrient choline.

Choline itself is a precursor in the synthesis of the neurotransmitter acetylcholine, the methyl donor betaine and phospholipids, including phosphatidylcholine and sphingomyelin among others. Phosphatidylcholine's role in the maintenance of cell-membrane integrity is vital to all of the basic biological processes. These are: information flow that occurs within cells from DNA to RNA to proteins; the formation of cellular energy and intracellular communication or signal transduction. Choline is an essential component of phospholipids, and is the building block for acetylcholine, a major neurotransmitter of the central nervous system. When a declining choline level becomes a limiting factor in the synthesis of acetylcholine, which can occur during exercise and other stressful activities, peak physical and mental performance can be affected. Choline has also been shown to potentiate the secretion of human growth hormone (hGH), a master hormone that in part regulates basal metabolism and hence body composition. Since the intrinsic release of hGH declines significantly after adolescence, manifestations are seen as diminished resistance to illness, vitality, and recovery, losses in muscle mass, increases in fat mass, and negative changes in sleep patterns.

Phosphatidylcholine, particularly phosphatidylcholine rich in polyunsaturated fatty acids, has a marked fluidizing effect on cellular membranes. Decreased cell-membrane fluidization and breakdown of cell-membrane integrity, as well as impairment of cell-membrane repair mechanisms, are associated with a number of disorders, including liver disease, neurological diseases, various cancers and cell death.

The further inclusion of additional sources of choline and phosphatidyl containing compounds is anticipated as yielding enhanced efficacy and benefits themselves as recognized in the art for a wide range of psychiatric, brain, and other functional benefits. Exemplary compounds include phospatidylserine, alpha-glyceryl phosphoryl choline, and choline citrate. Scientific research and clinical investigations have shown that phospatidylserine, for example, plays a critical role in maintaining optimal mental performance.

The further addition of pH modifiers including sodium acid sulfate, citric acid, ascorbic acid, gluconic acid or combinations thereof may improve the oxidative stability. The yet further addition of chelating agents including citric acid may also enhance the oxidative stability. Although citric acid controls the conversion of sucrose to invert sugar, accelerated storage conditions (i.e., a temperature of 60 degrees C. for more than 7 days) can lead to the formation of invert sugar (a mixture of glucose and fructose). A preferred pH modifier is sodium acid sulfate, which has the unique benefit of having minimal bitter flavor notes, otherwise associated with low pH. This is an important criteria, as solubility of the polycationic casein phosphopeptide and chitosan complexes is enhanced at lower pH. Enhanced solubility may reduce the chalkiness associated with precipitated compounds, an important criteria in the inclusion of the nanoemulsions in functional foods, confectioneries, and beverages for superior texture and mouthfeel.

In a specific embodiment, the invention includes a nanoemulsion composition having ingredients selected from the group of: non-reducing sugars, sugar polyols, or combinations thereof; modified starches; polysaccharides; glycerides selected from enzymatically modified oils, fats, and fatty acids of mono-, di-, and tri-glycerides; glycerides selected from lipolyzed modified oils, fats, and fatty acids of mono-, di-, and tri-glycerides; fruit concentrate sweetener as humectant that comprises a blend of hydrolyzed starch having a dextrose equivalent (D.E.) of up to approximately 25; fruit juice or fruit syrup concentrate of at least approximately 40% soluble solids and approximately 0% insoluble solids thereby forming a liquor having a dry weight composition of approximately 40 to approximately 65% complex carbohydrates; and approximately 35 to approximately 55% simple sugars from the fruit juice or fruit syrup concentrate; and approximately 0 to approximately 5% nutritional components occurring naturally in the fruit juice or fruit syrup concentrate; cocoa powder; Sucralose; or combinations thereof.

Cocoa powder contains around 20% raw protein. Maillard reactions are initiated by a condensation between the free amino group of amino acid, peptide, or protein and the carbonyl group of a reducing sugar to give a N-substituted glycosyl-amino compound followed by the reversible formation of the Schiff base, which cyclizes to the NB substituted glycosylamine and its then converted into the Amadori compound. The Amadori rearrangement is catalyzed by weak acids and is considered the key step of the Maillard reaction. Amadori compounds formed during the early stage of the Maillard reaction are responsible for the loss of nutritional value of amino acids and proteins, because their biological activity is reduced by the formation of Amadori compounds. Cocoa powder also contains around 10% polyphenols, which have antioxidative effects (Dreosti I. E. in Nutrition 16, 692-694 (2000)). The ability of cocoa powder to inhibit lipid oxidation in O/W emulsion systems with added sucrose (pH 6.6) is influenced by heat treatments. An extensive acid hydrolysis of sucrose, by heat, is detrimental to the antioxidant capacity of cocoa powder. However, for formulated O/W emulsions that have sorbitol (pH 6.6), cocoa powder shows enhanced oxidative stability upon storage at 60 degrees C. for 28 days.

A wide range of products may be manufactured by inclusion of the nanoemulsion compositions of the invention including: hypercholesterolemia prevention products in a mammal including salts selected from the group of calcium and magnesium salts; bone mineral loss prevention products in a mammal including salts selected from the group of calcium and magnesium salts; oils rich in Omega-3 products, further comprised of salts selected from the group of calcium and magnesium salts; oil-soluble flavor products; oil-soluble vitamin, nutraceutical, or pharmaceutical products; products having vegetable oils including rice bran oil, flax, chia, hemp, castor, soybean, lesquerella, dehydrated castor oil, rich in Omega-3, or conjugated linoleic acid, animal oils including fish, egg, poultry, and beef oils rich in Omega-3, or conjugated linoleic acid, or combinations thereof; microalgae oils, rich in Omega-3, or conjugated linoleic acid, or combinations thereof; beverage products being transparent including salts selected from the group of calcium and magnesium salts; cocoa products having improved creaminess, reduced bitterness, and reduced oxidation; protein rich products including high-methoxyl pectins or pectin alginates or combinations thereof having reduced protein settling and sedimentation; protein rich products having reduced protein settling and sedimentation; oil-in-water micro- and nano-emulsions having increased emulsion and oxidation stability; or water-in-oil micro- and nano-emulsions having increased emulsion and oxidation stability.

Additional preferred actives include actives that further enhance transport through cellular membranes/mitochondria. One exemplary is Acetyl L-Carnitine, an amino acid-like compound related to choline. It is a brain support supplement that may assist in the conversion of choline into acetylcholine, one of the body's key neurotransmitters. Additional L-carnitine components include components selected from the group consisting of free L-carnitine, L-carnitine L-tartrate, L-carnitine magnesium citrate and acetyl-L-carnitine.

The acetyl group that is part of acetyl-L-carnitine contributes to the production of the neurotransmitter acetylcholine, which is required for mental function. Several double-blind clinical trials suggest that acetyl-L-carnitine delays the progression of Alzheimer's disease and enhances overall performance in some people with Alzheimer's disease. Alzheimer's research has been done with the acetyl-L-carnitine form, rather than the L-carnitine form, of this nutrient. L-carnitine is traditionally made in the body from the amino acids lysine and methionine, and is needed to release energy from fat. It transports fatty acids into mitochondria, though the body requires adequate lysine, methionine, vitamin C, iron, niacin, and vitamin B6 to produce carnitine.

Additional preferred actives include actives that suppress delta-5 desaturase enzyme. A more preferred active is sesame lignans, an extract from sesame seeds. A series of specific actives are found in sesame lignans including sesamin and sesamol. Sesame lignans suppress the enzyme (delta-5 desaturase) that converts DGLA into arachidonic acid. By blocking the undesirable enzyme (delta-5 desaturase), more DGLA is available for conversion into beneficial prostaglandin.

Yet further additional actives include permeation enhancers, with exemplaries including acylcarnitine, phosphatidylcholine, fatty acids (eicosapentaenoic acid (EPA), docosahexaenoic acid (DHA), oleic acid, capric acid, linoleic acid, and their monoglycerides), bile salts (cholate, taurocholate and derivatives), salicylates (3- or 5-methoxy-salycilate, salicylate), homovanilate, surfactants (sodium dodecyl sulfate (SDS), Triton X-100, Brij), chelating agents (ethylenediamine tetraacetic acid (EDTA), citric acid, phytic acid, enamine derivatives), and aprotinin.

The inclusion of such permeation enhancers, in combination with the small size of the nanoemulsion composition enables permeation through various administration routes including the skin, blood capillary or membrane barriers. Therefore, the nanoemulsion composition is suitable for dermal, peroral, enteral, parenteral, ocular, pulmonary, and transmucosal administration routes. The term "permeation enhancer" includes all actives and methods that promote permeation through the cellular membranes, such as mitochondria of cells including, though not limited to, gastrointestinal, and brain cells.

Additional functionality includes enhancing cognitive performance, and reducing disorders of mental health. The use of specific actives such as cholines and serines is recognized in the art for the treatment of a wide range of cognitive and mental health disorders. These include as one exemplary, though not limited, enhancing memory functions in Alzheimer patients. The present invention uniquely achieves a synergistic impact on such cognitive and mental health conditions by enhancing the delivery of such actives and concurrently the delivery of omega-3. The realized benefits are greater than each individual component.

The range of products include, but are not limited to, confectionery, baked goods, spreads, dressings, salad dressings, nutraceutical supplements, functional foods products, ice cream, seed milks, dairy products, pharmaceutical tablets, syrups, and medicines, functional confectionery products, mineral-enriched drinks, and oral care products. The specific complexation of casein phophopeptide with chitosan further leverages the bioadhesive properties of chitosan, thus the complex may provide both superior solubility for the calcium and adhesion to the teeth both of which are required conditions for teeth remineralization.

Compositions of the present invention may include O/W and W/O emulsions prepared with vegetable and animal oils that contain a significant amount of highly polyunsaturated fatty acids such as rice bran oil, flaxseed oil, chia oil, hemp oil, soybean oil, lesquerella oil, castor oil, dehydrated castor oil, menhaden oil, sardine oil, herring oil, salmon oil, anchovy oil, and other oils rich in Omega-3, or conjugated linoleic acid. The oil content of the O/W and W/O emulsions may vary according to the oil species component used and other components but may be within the range of 0.1-95 w/v %, preferably 1-85 w/v %. Embodiments of the present invention also may be effective when applied to oil flavors such as fruit and herb flavored oils, cheese flavored oils, butter flavored oils, and oil soluble vitamin, nutraceutical or pharmaceutical products.

Oil-in-water (O/W) emulsions that include small lipid droplets dispersed in an aqueous medium form the basis of many kinds of foods, e.g., milk, cream, beverages, dressings, dips, sauces, batters and deserts. Emulsions are thermodynamically unstable systems because of the unfavorable contact between oil and water phases, and because the oil and water phases have different densities, hence they will always breakdown over time. Use of emulsifiers, which are surface-active ingredients that absorb to the surface of freshly formed lipid droplets during homogenization, usually retards emulsion breakdown. Once absorbed, they facilitate further droplet disruption by lowering the interfacial tension, thereby reducing the size of the droplets produced during homogenization. Emulsifiers also reduce the tendency for droplets to aggregate by forming protective membranes and/or generating repulsive forces between the droplets. A good emulsifier should rapidly adsorb to the surface of the lipid droplets formed during homogenization, rapidly lower the interfacial tension by a significant amount and protect the droplets against aggregation during emulsion processing, storage and utilization.

Emulsions prepared with egg yolk phospholipids and the nanoemulsion compositions of the present invention have improved stability against phase separation and particle aggregation. Recent studies for the purpose of enhancing flavor release have shown that the release of non-polar flavors from O/W emulsions during mastication is controlled by encapsulating the oil droplets within biopolymer particles (Malone et al. in Flavor Release, ACS Symposium Series, American Chemical Society, pp. 212-217 (2000)). Biopolymer particles are created by the caprine caseinophosphopeptide-chitosan complex and eggplant-carrageenan complex that are embodiments of the inventive antioxidant compositions.

The caseinophosphopeptide employed as nanoemulsion compositions of the present invention may include alpha.sub.s2-casein as isolated from caprine (goat) milk. Caseins and caseinophosphopeptides exhibit different degrees of phosphorylation, and a direct relationship between the degree of phosphorylation and mineral chelating activity has been described (Kitts, D. D. in Can. J. Physiol. Pharmacol. 72, 423-434 (1994)). Accordingly based on phosphorylation, alpha.sub.s2-casein>alpha.sub.s1-casein>beta-casein>kappa-casein. Caseinophosphopeptide isolated from caprine (goat) milk high in alpha.sub.s2-casein (alpha.sub.s2-casein=29.2% of total casein) has more mineral chelating activity than a caseinophosphopeptide isolated from bovine (cow) milk (alpha.sub.s2-casein=12.1% of total casein). The phosphoric group of phosphoserine and carboxic groups of acidic amino acids present in the caseinophosphopeptide isolated from caprine (goat) milk high in alpha.sub.s2-casein, without being bound by theory, likely complexes with metal ions such as iron and copper. Complexation with other critical nutritional minerals, such as selenium, zinc, and magnesium may further increase their bioavailability.

It would be understood to one skilled in the art that other milk high in alpha.sub.s2-casein may be suitable for the present invention. Choice of milk may be influenced, inter alia, by economic factors and availability of particular milk. The selection of milk containing high levels of alpha.sub.s2-casein, which is low in alpha.sub.s1-casein, may be carried out by reversed-phase high performance liquid chromatography (RP-HPLC) (Mora-Gutierrez et al. in J. Dairy Sci. 74, 3303-3307 (1991)). The casein composition of the caprine caseinophosphopeptide is normally as follows: alpha.sub.s2-casein content=29.2%, alpha.sub.s1-casein content=5.9%; beta-casein content=50.5% and kappa-casein content=14.4%.

The fat in caprine (goat) milk is also rich in medium-chain triglycerides (MCT) (C6:0 Caproic, C8:0 Caprylic and C10:0 Capric) which are absorbed in the proximal intestine and do not require bile salts to be absorbed (Vanderhoof et al. in J. Parenter. Enteral Nutr. 8, 685-689 (1984)). These MCT have become of considerable interest to the medical profession because of their unique benefits in many metabolic diseases of humans (Babayan V. K. in J. Amer. Oil Chem. 59, 49A-51A (1981)). The bone (femur and sternum) is the preferential organ for the deposit of magnesium in animals fed a caprine (goat) milk diet, which has been ascribed to its special characteristics concerning lipid composition (rich in MCT) (Lopez-Aliaga et al. in J. Dairy Sci. 86, 2958-2966 (2003)). Lipids are associated with proteins (caseins) in milk and their content in bound lipid fractions is high (Cerbulis J. in J. Agric. Food Chem. 15, 784-786 (1967)). The MCT content of the caprine caseinophosphopeptide used in this inventive antioxidant composition is high because this caprine caseinophosphopeptide is produced from caprine (goat) milk with a fat content of 1% by enzymatic hydrolysis and acid precipitation with chitosan. Chitosan, which assumes a polycationic character at acidic pH, exhibits a high fat-binding capacity (No et al. in J. Food Sci. 65, 1134-1137 (2000)).

In an exemplary embodiment of the invention, caprine (goat) milk (1% fat content) characterized by a high alpha.sub.s2-casein content is used as the starting material in a method of the present invention: (a) digesting the casein present in caprine (goat) milk high in alpha.sub.s2-casein with 0.01% (w/v) trypsin (enzymatically modified proteins through trypsin digestion) at a substantially neutral pH to produce a crude caseinophosphopeptide, (b) reducing the pH to 4.5 with 2% (w/v) chitosan (SEACURE L 110 with 70% deacetylation; Pronova Biopolymer, Inc., Oslo, Norway) dissolved in 10% citric acid (w/v), (c) removing the unreacted casein from the supernatant by centrifugation, (d) permitting the supernatant to stand for 20 hours at 4 degrees C., (e) adjusting the pH of the supernatant to about 6.0, then adding calcium chloride (0.2% w/v) and ethanol (40% v/v), to precipitate a calcium-bound caseinophosphopeptide, which is recovered by centrifugation. This calcium-bound caseinophosphopeptide may be washed with deionized water and dried by lyophilization. The composition of the lyophilized product is provided in Table 1.

TABLE 1

| Caprine caseinophosphopeptide composition | Per 100 grams |
|---|---|
| Kjeldahl N | 6.49 |
| Calcium | 8.61 |
| Phosphorus | 2.76 |
| Medium-chain triglycerides | 9.71 |

A food grade acidulent may be added to the fat emulsion before adding the acid-soluble caprine caseinophosphopeptide. The acid-soluble caprine caseinophosphopeptide may be added to an acidic environment ranging from approximately pH 2.0 to 5.7. The food grade acidulent may be citric acid, ascorbic acid, gluconic acid, and mixtures thereof. The acidulent in the fat emulsion may be mostly citric acid. Citric acid sequesters deleterious trace metals, particularly copper and iron, which hasten deterioration of color, flavor and vitamin A content.

As used herein, the term LBJ refers to a mixture of sugars and soluble fiber derived from eggplant (*Solanum melongena*). To produce LBJ in one example, whole eggplant is slurried with water to which citric acid and iota-carrageenan are added. This mixture is reacted at elevated temperature under controlled conditions for a specific period of time. The resulting slurry of sugars/soluble fiber (LBJ) is subsequently treated with an adsorptive resin functional to remove from the sugars/soluble fiber (LBJ) bitter taste components, color and odor components. The treated sugars/soluble fiber (LBJ) solution may be concentrated and dried if desired to powder form. The further addition of polyphenols, specifically the polyphenols derived from the fruit of *Solanum melongena* is possible.

More specifically, in an exemplary embodiment, an aqueous solution containing 0.50% citric acid and 0.25% iota-carrageenan is heated at 45 degrees C. for 6 hours with continuous stirring. Eggplant samples may be obtained from local food stores or any other source and stored under refrigeration at approximately 4 degrees C. until use if necessary. About one hour prior to use, the eggplant samples are removed from refrigeration and equilibrated at room temperature at about 22 degrees C. The eggplants (0.7 kg) are rinsed with water, peeled and then sliced into 4-5 mm thick slices. These are immediately immersed in a treatment bath containing the mixed-acid solution of citric acid and iota-carrageenan. The treatment bath with the sliced eggplants and mixed-acid solution of citric acid and iota-carrageenan is then heated to a temperature that may be in the range 70 degrees C. to 80 degrees C., typically 75 degrees C. This elevated temperature may be maintained for at least 2 hours but possibly held at such elevated temperature for longer, e.g., about 4 hours, and then cooled to between 0 degrees C. and 50 degrees C., in a particular embodiment about 4 degrees C., for a period of time, typically about 12 hours. Finally, the mixture is decanted through Whatman No. 4 filter paper or similar filtration medium.

In an exemplary embodiment, the aqueous slurry/solution (LBJ) is passed through a column of an adsorptive resin. The adsorptive resin may be a polymeric resin, which functions to remove bitterness, odor and color from the aqueous slurry/solution (LBJ). One suitable class of adsorptive resins for use are polymeric cross-linked resins composed of styrene and divinylbenzene such as, for example, the Amberlite series of resins, e.g., Amberlite XAD-2, Amberlite XAD-4 and Amberlite XAD-16, which are available commercially from Supelco of Bellefonte, Pa. Other polymeric crosslinked styrene and divinylbenzene adsorptive resins suitable for use according to the invention are XFS-4257, XFS-4022, XUS-40323 and XUS-40322 manufactured by Dow Chemical Company of Midland, Mich., and other similar resins.

Treatment of the aqueous slurry/solution (LBJ) in accordance with this invention may be conducted in various manners such as by a batch treatment or by passing the aqueous slurry/solution (LBJ) through a column containing the adsorptive resin. The column size selected depends upon the sample size and the concentration of the aqueous slurry/solution (LBJ).

More specifically, in an exemplary embodiment, a batch of approximately 100 g of Amberlite XAD-2 is slurried in water and poured into an open glass chromatography column (2×30 cm) fitted with a Teflon stopcock. The column is then prepared for use by washing it with two liters of twice-distilled water, two liters of distilled methanol (reagent grade), and finally two liters of distilled water. The aqueous slurry/solution (LBJ) treated in the column may preferably be free of insoluble material so as to not plug the column or impede flow. Generally, the concentration of eggplant undergoing treatment may be in the range of about 50 to 70% by weight. The pH of the slurry/solution (LBJ) may be in the range of pH 3 to 4. The flow rate of the aqueous slurry/solution (LBJ) through the column may preferably be slow enough to allow sufficient time for the undesired bitterness, color and odor to be adsorbed in the adsorptive resin. Column flow rates between one to five bed volumes/hour are generally satisfactory.

One aqueous slurry/solution (LBJ) according to the present invention contains a fructose portion of 3.7% and a sucrose portion of 1.5% as determined by high-performance liquid chromatography (HPLC). Thus, this natural composition exhibits a high hygroscopic property. Saccharide polymers may be used as spray-drying aids in the manufacture of this natural composition. The composition may include between around 5 and 10% by weight maltodextrin. The maltodextrin may have a low DE, generally not exceeding about 10. The aqueous slurry/solution (LBJ) is mixed with maltodextrin DE=10 at a concentration of 6% (by weight) after the aqueous slurry/solution (LBJ) is passed through a column of the adsorptive resin. Then, the aqueous slurry/solution (LBJ 10) is dried by spray drying or the like to provide a product that is well suited for use as a natural antioxidant ingredient for fat emulsions. The composition of this product is provided in Table 2.

TABLE 2

| LBJ 10 physicochemical composition | Per 100 grams |
| --- | --- |
| carbohydrate portion | 92.21 |
| nitrogen content | 0.71 |
| fat portion | 0.16 |

TABLE 2-continued

| LBJ 10 physicochemical composition | Per 100 grams |
| --- | --- |
| ash portion | 2.33 |
| dietary fiber portion | 0.41 |
| soluble fiber portion | 0.41 |
| fructose portion | 3.72 |
| glucose portion | 4.26 |
| sucrose portion | 1.48 |
| maltose portion | 2.19 |
| sugar portion | 11.65 |

The numerical values for carbohydrate, crude protein, fat portion, ash portion, dietary fiber portion, soluble fiber portion, and sugar portion are those according to a general analysis.

Carrageenans exhibit thickening or viscosity-increasing effect. The viscosity of the LBJ 10 composition of Table 2, which has 0.25% iota-carrageenan, is rather low, i.e., about 11 cps (1%, 22 degrees C.), and it tastes slightly sweet and is odorless. Carrageenans such as kappa-carrageenan and lambda-carrageenan can also be used in the preparation of LBJ 10. Carrageenans are known to interact with casein (and derived phosphopeptides) to modify food texture by improving water holding capacity (Mora-Gutierrez et al. in J. Agric. Food Chem. 46, 4987-4996 (1998)). In some embodiments of the invention, the combination of egg yolk phospholipids, caprine caseinophosphopeptide and LBJ 10 impart richness, lubricity and creaminess to fat-reduced emulsions. Because antioxidant activities are correlated with the phenolic contents of foods, the total phenolic content of LBJ 10 was determined using methods described by Singlenton et al., Analysis of Total Phenols and Other Oxidation Substrates and Antioxidants by Means of Folin-Ciocalteu Reagent, Methods in Enzymology, Oxidants and Antioxidants, 1998, pp. 152-178. The total phenolic content of LBJ 10 was 45 μmol gallic acid equivalents/g of LBJ 10.

The present invention includes compositions of natural antioxidants including tocopherols, beta-carotene, egg yolk or soybean phospholipids, sucrose or sorbitol, caprine caseinophosphopeptide, eggplant (LBJ 10), and citric acid. Specific antioxidant ingredients of the present invention may include from about 0.01 to about 0.03% by lipid content of tocopherols, from about 0.01 to about 0.03% by lipid content of beta-carotene, from about 0.05 to about 0.5% by weight of emulsion of egg yolk or soybean phospholipids, from about 2 to about 20% by weight of emulsion of sucrose or sorbitol, from about 0.01 to about 0.05% by weight of emulsion of caprine caseinophosphopeptide, from about 0.01 to about 0.2% by weight of emulsion of eggplant (LBJ 10), and from about 0.05 to about 0.5% by weight of emulsion of citric acid.

One specific composition includes about 0.01% tocopherols, 0.01% beta-carotene, 0.1% egg yolk or soybean phospholipids, 10% sorbitol, about 0.05% caprine caseinophosphopeptide, about 0.1% eggplant (LBJ 10), and about 0.5% citric acid, all by weight of emulsion.

Unrefined Canadian flaxseed oil is rich in tocopherols and beta-carotene. A specific embodiment of the composition of the present invention, especially effective for O/W emulsions prepared with Canadian flaxseed oil, is as follows: 0.05% caprine caseinophosphopeptide, 0.01% eggplant (LBJ 10), and 0.5% citric acid.

The fat emulsion may be produced by conventional technology. An exemplary production process includes adding egg yolk or soybean phospholipids in suitable amounts to a predetermined amount of the oil component, homogenizing the mixture, adding sorbitol, caprine caseinophosphopeptide, eggplant (LBJ 10), and citric acid in suitable amounts to a predetermined amount of the water component, and emulsifying the entire mixture with a homogenizing machine such as the conventional homo-mixer, homogenizer, ultrasonic homogenizer, or pressure homogenizer. The mixture may preferably be finely dispersed by homogenization to ensure a homogeneous equal dispersion of the natural antioxidant composition in all the oil particles. The average particle diameter of the fat emulsion particles is within the range of 5-50 nm. The emulsified mixture may be pasteurized using conventional methods.

Some natural antioxidant compositions of the present invention may exhibit antioxidant activity superior to prior compositions or synthetic antioxidants. Some natural antioxidant compositions of the present invention may also offer a number of health benefits, including helping to promote bone health by boosting calcium and magnesium absorption, and a healthy cardiovascular system by lowering blood serum cholesterol levels. Thus in certain embodiments, the amount of caprine caseinophosphopeptide and eggplant (LBJ 10) may range from the minimum amount which will stabilize the oil against oxidation, or effectiveness, to at least that amount which will promote bone health and protect against heart disease in animal or human bodies. In general, the amount of caprine caseinophosphopeptide and eggplant (LBJ 10) used may range from 0.01 to 0.05% by weight for caprine caprine caseinophosphopeptide and 0.01% to 0.1% by weight for eggplant (LBJ 10).

EXAMPLES

The following examples are included to demonstrate specific embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Examples 1 Through 3 Demonstrate Omega-3 Nanoemulsions with a Range of Synergistic Actives.

The health benefits of some embodiments of the present invention are explained in detail in Examples 4 through 6.

Example 1

O/W Nanomulsion Containing Sorbitol and Egg Yolk Phospholipids

DHA rich oil (30 mL), sorbitol (10 g), trehalose (2 g), egg yolk phospholipids (0.1 g), sesame lignans (0.03 g), Coenzyme Q.sub.10-gamma-cyclodextrin complex (0.5 g), and deionized water (56.2 mL) are homogenized for 2 minutes with a hand-held Biohomogenizer Mixer (Biospec Products, Inc., Bartlesville, Okla.). Additionally 0.05% caprine caseino-phosphopeptide, 0.01% eggplant (LBJ 10), 0.0020% gallic acid, 1% 0.1 N potassium hydroxide, and 0.1% choline citrate were added to the O/W emulsion followed by homogenization for 2 minutes (Sample A). An O/W emulsion (30% DHA) emulsified with egg yolk phospholipids (0.1%) and containing sorbitol (10%), trehalose (2%), Coenzyme Q.sub.10-gamma-cyclodextrin complex (0.5%), 0.1 N potassium hydroxide (1%), choline citrate (0.1%), and deionized water (56.3%) was homogenized for 4 minutes and used as the control (Sample B). The coarse emulsions were then homogenized three times at 5000 psi through a high-pressure valve, two-stage APV Lab 1000 homogenizer (Albertslund, Denmark). The particle size of the nanoemulsions was 5.8 microns. The nanoemulsions were stored in dark Pyrex bottles at 60 degrees C. during 28 days. At 60 degrees C. temperature hastened the rate of oxidation and at the same time encouraged progression of ambient temperature oxidative mechanisms and minimized artifact forming reactions. (See Frankel E. N., In Search of Better Methods to Evaluate Natural Antioxidants and Oxidative Stability in Food Lipids, Trends in Food Sci. Technol. 1993, Vol. 4, pp 220-225). The nanoemulsions were subjected to peroxide value (PV) and p-anisidine value (AV) determination analyses. The antioxidant activity of the composition according to an embodiment of the present invention is demonstrated by the results in Table 3.

TABLE 3

Peroxide values [meq/kg] and p-anisidine values of the O/W nanoemulsions containing DHA during 28-days storage at 60 degrees C.

| Sample | Peroxide Value | p-Anisidine Value |
|---|---|---|
| Sample A | 0.76 | 1.79 |
| Sample B | 39.20 | 5.48 |

The results given in Table 3 show clearly the antioxidant effectiveness of the composition (Sample A) according to an embodiment of the present invention.

Example 2

O/W Nanomulsion Containing Sorbitol and Soybean Phospholipids

DHA rich oil (30 mL), sorbitol (10 g), trehalose (2 g), soybean phospholipids (0.1 g), acetyl L-carnitine (0.03 g), CoQ10-gamma-cyclodextrin complex (0.5%), and deionized water (56.2mL) were homogenized for 2 minutes with a hand-held Biohomogenizer Mixer (Biospec Products, Inc., Bartlesville, Okla.). Additionally 0.05% caprine caseinophosphopeptide, 0.01% eggplant (LBJ 10), 0.0020% gallic acid, 1% 0.1 N potassium hydroxide, and 0.1% choline citrate were added to the O/W emulsion followed by homogenization for 2 minutes (Sample A). An O/W emulsion (30% DHA) emulsified with soybean phospholipids (0.1%) and containing sorbitol (10%), trehalose (2%), CoQ10 -gamma-cyclodextrin complex (0.5%), 0.1 N potassium hydroxide (1%), choline citrate (0.1%), and deionized water (56.3 mL) was homogenized for 4 minutes and used as the control (Sample B). The coarse emulsions were then homogenized three times at 5000 psi through a high-pressure valve, two-stage APV Lab 1000 homogenizer (Albertslund, Denmark). The particle size of the nanoemulsions was 5.6 microns. The nanoemulsions were stored in dark Pyrex bottles at 60 degrees C. during 28 days. At 60 degrees C. temperature hastened the rate of oxidation and at the same time encouraged progression of ambient temperature oxidative mechanisms and minimized artifact forming reactions. (See Frankel E. N., In Search of Better Methods to Evaluate Natural Antioxidants and Oxidative Stability in Food Lipids, Trends in Food Sci. Technol. 1993, Vol. 4, pp 220-225). The nanoemulsions were subjected to peroxide value (PV) and p-anisidine value (AV) determination analyses. The antioxidant activity of the composition according to an embodiment of the present invention is demonstrated by the results in Table 4.

TABLE 4

Peroxide values [meq/kg] and p-anisidine values of the O/W nanoemulsions containing DHA during 28-days storage at 60 degrees C.

| Sample | Peroxide Value | p-Anisidine Value |
|---|---|---|
| Sample A | 0.85 | 1.34 |
| Sample B | 27.46 | 5.02 |

The results given in Table 4 show clearly the antioxidant effectiveness of the

The results given in Table 4 show clearly the antioxidant effectiveness of the composition (Sample A) according to an embodiment of the present invention.

Example 3

A Chocolate-Flavored, O/W Nanoemulsion Containing Sorbitol and Egg Yolk Phospholipids Cocoa mix (2 g), DHA rich oil (30 mL), sorbitol (10 g), trehalose (2 g), egg yolk phospholipids (0.1 g), conjugated linoleic acid (0.3 g), CoQ10-gamma-cyclodextrin complex (0.5 g), and deionized water (53.9 mL) were homogenized for 2 minutes with a Biohomogenizer Mixer (Biospec Products, Inc., Bartlesville, Okla.). Additionally 0.05% caprine caseino-phosphopeptide, 0.01% eggplant (LBJ 10), 0.01% gallic acid, 1% 0.1 N potassium hydroxide, and 0.1 % choline citrate were added to the O/W emulsion followed by homogenization for 2 minutes (Sample A). An O/W emulsion (30% DHA) emulsified with egg yolk phospholipids (0.1%) and containing cocoa mix (2%), sorbitol (10%), trehalose (2%), conjugated linoleic acid (0.3%), CoQ10 -gamma-cyclodextrin complex (0.5%), 0.1 N potassium hydroxide (1%), choline citrate (0.1 %), and deionized water (54.0 mL) was homogenized for 4 minutes and was used as the control (Sample B). The coarse emulsions were then homogenized three times at 5000 psi through a high-pressure valve, two-stage APV Lab 1000 homogenizer (Albertslund, Denmark). The particle size of the nanoemulsions was 5.9 microns. The nanoemulsions were stored in dark Pyrex bottles at 60 degrees C. during 28 days. At 60 degrees C. temperature hastened the rate of oxidation and at the same time encouraged progression of ambient temperature oxidative mechanisms and minimized artifact forming reactions. (See Frankel E. N., In Search of Better Methods to Evaluate Natural Antioxidants and Oxidative Stability in Food Lipids, Trends in Food Sci. Technol. 1993, Vol. 4, pp 220-225). The nanoemulsions were subjected to peroxide value (PV) and p-anisidine value (AV) determination analyses. The antioxidant activity of the composition according to an embodiment of the present invention is demonstrated by the results in Table 5.

TABLE 5

Peroxide values [meq/kg] and p-anisidine values of the O/W nanoemulsions containing DHA during 28-days storage at 60 degrees C.

| Sample | Peroxide Value | p-Anisidine Value |
|---|---|---|
| Sample A | 1.07 | 1.55 |
| Sample B | 32.69 | 5.86 |

The results given in Table 5 show clearly the antioxidant effectiveness of the composition (Sample A) according to an embodiment of the present invention.

Example 4

Cholesterol-Lowering Activity in Rats

Rats (Sprague-Dawley type, 7 weeks of age, male) were fed a diet low in calcium and high in animal fat. These rats were divided into three groups each being formed of 12 rats having a similar mean body weight of 200-205 grams, then three kinds of heat-sterilized O/W nanoemulsions i.e., an O/W nanoemulsion of 0.05 % (w/v) caprine caseinophosphopeptide and 0.01 % (w/v) eggplant (LBJ 10) supplemented with calcium (300 ppm), an O/W nanoemulsion supplemented with calcium (300 ppm), and an O/W nanoemulsion non-supplemented with calcium were respectively given from feeding bottles to the rats as drinking water. Composition of these O/W nanoemulsions was identical in terms of flaxseed oil (1 g/L), soybean phospholipids (0.1 g/L), sucrose (4 g/L), and citric acid (5.0 g/L) content. O/W nanoemulsions were supplemented with calcium gluconate (3 g/L).

The three groups of rats were free to take the feed and water in, during the treatment period of 21 days. At the end of the 21-day, rats were deprived of food overnight and anesthetized by intraperitoneal injection of sodium pentobarbital (40 mg/kg body weight). Blood collection was carried out from cardiac puncture. With respect to analysis, measurements were carried out using a DU-530 Spectrophotometer made by Beckman by means of a colorimetric method.

Results of the measurement for blood serum total cholesterol are shown in Table 6.

TABLE 6

| Group | Cholesterol, mg/dL |
|---|---|
| Control (non-supplemented) | 84.92 ± 7 |
| Control (supplemented) | 78.36 ± 5 |
| Natural antioxidant composition (supplemented) | 67.30 ± 4 |

According to the above results, it has been proved that the increase in serum cholesterol of male Sprague-Dawley rats fed a low calcium and high animal fat diet has been lowered by the addition of an antioxidant composition according to an embodiment of the present invention (caprine caseinophosphopeptide combined with eggplant (LBJ 10) and citric acid at levels of 0.05% (w/v), 0.01% (w/v), and 0.5% (w/v), respectively) to a calcium-supplemented O/W emulsion.

This natural antioxidant composition, therefore, can be applied to O/W nanoemulsions as physiologically functional factor.

Example 5

Calcium and Magnesium Bioavailability in Rats

Rats (Sprague-Dawley type, 7 weeks of age, male) were fed an egg white-diet low in calcium. Chromic oxide ($Cr_2O_3$, 0.5 g/kg diet), an insoluble and unabsorbed marker, was added to the egg white-diet to allow estimation of apparent Ca and Mg absorption by determining the ratio of Ca:Cr and Mg:Cr in the diet and feces. These rats were divided into four groups each being formed of 12 rats and having a similar mean body weight of 200-205 grams, then three kinds of heat-sterilized O/W nanoemulsions i.e., an O/W nanoemulsion of 0.05 % (w/v) caprine caseinophosphopeptide and 0.01 % (w/v) eggplant (LBJ 10) supplemented with calcium (300 ppm), an O/W nanoemulsion supplemented with calcium (300 ppm), and an O/W nanoemulsion non-supplemented with calcium were respectively given from feeding bottles to the rats as drinking water. Composition of these O/W nanoemulsions was identical in terms of flaxseed oil (1 g/L), soybean phospholipids (0.1 g/L), sucrose (4 g/L), and citric acid (5.0 g/L) content. O/W nanoemulsions were supplemented with calcium gluconate (3 g/L).

The three groups of rats were free to take the feed and water in, during the treatment period of 21 days. Food intake was measured every day. Feces were collected during the last 3 days and freeze-dried. At the end of the 21-day, rats were deprived of food overnight and anesthetized by intraperitoneal injection of sodium pentobarbital (40 mg/kg body weight). The right femurs were excised for measurement of Ca, and Mg content. The amounts of Ca, Mg, and Cr in the diets and feces were quantified by atomic absorption spectrometry (Varian Analytical Instruments, Walnut Creek, Calif.) after wet-ashing with an acid mixture (16 mol/L $HNO_3$:9 mol/L $HClO_4$=3:1). The right femurs were treated with $1N$ $HNO_3$ and ashed at 550 degrees C. Ca and Mg content were determined in the same manner as in the case of the diets and feces. Apparent Ca absorption was calculated by the following formula: Apparent Ca absorption (%)=100[(Ca intake/Cr intake)−(Ca in the feces/Cr in the feces)]/(Ca intake/Cr intake). Apparent Mg absorption was calculated in a similar manner.

The apparent Ca and Mg absorption, and femoral bone Ca and Mg content of rats fed the three different O/W nanoemulsions are shown in Table 7.

TABLE 7

| Group | Apparent Ca absorption (%) | Apparent Mg absorption (%) | Bone Ca content (mg/femur) | Bone Mg content (mg/femur) |
|---|---|---|---|---|
| Control (non-supplemented) | 49 ± 5.7 | 51 ± 4.2 | 89.63 ± 0.27 | 4.47 ± 0.13 |
| Control (supplemented) | 54 ± 6.0 | 49 ± 5.1 | 97.08 ± 0.19 | 4.31 ± 0.27 |
| Antioxidant Composition (supplemented) | 59 ± 5.0 | 61 ± 5.9 | 103.20 ± 0.14 | 5.62 ± 0.11 |

The data show enhanced Ca and Mg bioavailability from the O/W nanoemulsion containing an antioxidant composition according to an embodiment of the present invention.

Example 6

Bone Metabolism and Dynamic Strength of Bone in Rats

Rats (Sprague-Dawley type, 7 weeks of age, male) were fed a diet low in calcium. These rats were divided into four groups each being formed of 12 rats and having a similar mean body weight of 200-205 grams, then three kinds of heat-sterilized O/W nanoemulsions i.e., an O/W nanoemulsion of 0.05 % (w/v) caprine caseinophosphopeptide and 0.01 % (w/v) eggplant (LBJ 10) supplemented with calcium (300 ppm), an O/W nanoemulsion supplemented with calcium (300 ppm), and an O/W nanoemulsion non-supplemented with calcium were respectively given from feeding bottles to the rats as drinking water. Composition of these O/W nanoemulsions was identical in terms of flaxseed oil (1 g/L), soybean phospholipids (0.1 g/L), sucrose (4 g/L), and citric acid (5.0 g/L) content. O/W nanoemulsions were supplemented with calcium gluconate (3 g/L).

The three groups of rats were free to take the feed and water in, during the treatment period of 21 days. At the end of the 21-day, rats were deprived of food overnight and anesthetized by intraperitoneal injection of sodium pentobarbital (40 mg/kg body weight). The left femurs were collected from the animals and soft tissue was removed. The left femur from each animal was subjected to bone mineral content (BMC), bone mineral density (BMD), and bone mechanical strength (BMS) measurements using dual-energy X-ray absorptiometry (DEXA), which is a typical method used to study the status of bone growth. Table 8 shows the beneficial effects of an antioxidant composition according to an embodiment of the present invention on bone metabolism and dynamic strength of bone in rats.

TABLE 8

| Group | BMC (g) | BMD (g/cm2) | BMS (kg force) |
|---|---|---|---|
| Control (non-supplemented) | 0.1912 ± 0.012 | 0.1346 ± 0.004 | 8.402 ± 0.321 |
| Control (supplemented) | 0.2041 ± 0.012 | 0.1432 ± 0.004 | 8.591 ± 0.298 |
| Antioxidant composition | 0.2134 ± 0.012 | 0.1518 ± 0.004 | 9.567 ± 0.298 |

The data clearly indicate that the O/W nanoemulsion containing an antioxidant composition according to an embodiment of the present invention strengthens the femur bones in rats by enhancing the amount of magnesium retained in bone (Example 5), and that this results from increased apparent magnesium absorption (Example 5).

The caprine caseinophosphopeptide-chitosan-MCT bound complexes, which are present in the above antioxidant composition according to an embodiment of the present invention, are thermally stable and deliver large amount of magnesium to the proximal intestine, the site for magnesium absorption. Thus the complexes per se can provide physiological activity of magnesium to low-pH, protein-based beverages and transparent beverages processed by heat treatment. The complexes prevent protein sedimentation in low pH (3.5-4.2) beverages when used in combination with high-methoxyl pectins or pectin alginates.

Example 7

Transparent Low-pH (3.0-4.2) Beverages Containing Caprine Caseinophosphopeptide

A big factor in the drop in calcium and magnesium consumption in the US is the fact that soft drinks have replaced milk in the American diet. Milk is an excellent source of calcium (1,310 mg/L) and also contains magnesium (120 mg/L). A Consumer Beverage Consumption study conducted in late 2000, surveyed a total of 1,379 participants in two age groups-adults (19-64; 320 males/358 females) and teens (12-18; 326 boys/375 girls). Adults reported that their favorite beverage is "cold, refreshing, and satisfying" whereas teens prefer their drinks to be "cold, refreshing, and delicious". In this survey, teens and adults, milk drinkers and non-milk drinkers expressed comments regarding their concern with health issues, additives, chemicals, handling and spoilage.

A growing body of research now shows that the more soft drinks teenagers consume, the higher their risk of broken bones and, in later life, osteoporosis. Since 1970 Americans have more than doubled their soft drink consumption while drinking less milk. Consumers want a cold, refreshing, satisfying, portable, and healthy beverage. Caprine caseinophosphopeptide can be used in transparent low-pH (3.0-4.2) beverages fortified with calcium and magnesium to prevent the loss of these minerals from bone and therefore, lowering the risk of bone fractures.

Caprine caseinophosphopeptide can also form the building stones for mineral-fortified, low-pH beverages tailored for individuals with lactase non-persistence, a reduced capacity to metabolize lactose. The presence of lactose in milk is detrimental for those individuals that suffer from lactose intolerance. The ingestion of one to two glasses of milk can lead to abdominal discomfort and diarrhea in such individuals. Many studies have noted racial differences in the incidence of lactose intolerance. In the United States is estimated that only 10-15% of adult Caucasians react adversely to lactose, whereas 70% of adult Afro-Americans are lactose intolerance. The incidence of lactose intolerance in adult Asians is 95%. The beverage food industry could formulate a calcium- and magnesium-fortified beverage containing caprine caseinophosphopeptide to export to the Far East.

Example 8

Coated Nuts

Long shunned by dieters for their fat content, nuts have made a big-time dietary come back. Recent epidemiological studies suggest that frequent nut consumption may be protective against heart disease and other chronic diseases. As mentioned earlier, the level of fat in the diet influences magnesium absorption because fatty acids have a greater tendency to form soaps with calcium than magnesium (Van Dokkun et al. in Ann. Nutr. Metab. 27, 361-367 (1983)).

Recent research studies have shown that increased lipid proportion of the diet improves the digestive utilization of magnesium in clinical cases of malabsorption syndrome (Alfórez et al. in J. Dairy Res. 68, 451-461 (2001)). Increased proportions of protein in the diet also favors magnesium absorption (Pallar és et al. in J. Agric. Food Chem. 44, 1816-1820 (1996)). Nuts are rich in fat, protein, and magnesium. The inventive antioxidant composition promotes a significant increase of magnesium absorption, which is reflected in the greater quantity of this mineral stored in femoral bone. Magnesium is associated with strong bones. People who crunch on nuts coated with the inventive antioxidant composition can lower the risk of bone fractures.

Additional research post provisional

Additional testing has been performed using a variety of chitosan forms, resulting in the preferred chitosan which has trace amounts of iron. Alternatively, a pure form of chitosan can be complexed with iron with the resulting chitosan-iron complex being used to achieve comparable iron levels as present in the Pronova chitosan (i.e., less than 200 ppm). The more preferred chitosan is a non-shellfish source chitosan such as resulting from fermentation process of the fungi *Aspergillus niger*) as available from Cargill. The specifically preferred chitosan is a chitosan lactate. Chitosan as chitosan alpha lipoic acid is also a particularly potent component of the antioxidant and/or nanoemulsion composition. Thiolated chitosan is additionally a multifunctional chitosan form, that has the secondary benefit of being a superior bioadhesive and mucoadhesive. The superior calcium absorption, without being bound by theory, may be attributed to the increased mucoadhesive properties within the gastrointestinal tract yielding controlled release of the calcium casein phosphopeptide. It is anticipated that nanoemulsions of essentially any oil soluble materials, including difficult to solubilize hydrophobic molecules utilized as nutraceuticals or pharmaceuticals. A thiolated chitosan includes chitosan-4-thio-butyl-amidine (a.k.a. chitosan-TBA). The further addition of glutathione, most notably reduced glutathione, yields superior bioadhesive properties.

The further addition of CoQ10 also enhances the antioxidative stability of lipids, including within the inventive nanoemulsions. The more preferred CoQ10 is infused into the lipid prior to emulsion. The particularly preferred CoQ10 is modified through means known in the art, such as "encapsulation" into cyclodextrins as provided by Wacker in their Cavamax CoQ10 product, to be solubilized in the water phase of the emulsion. Thus, without being bound by theory, the CoQ10 migrates to be in closed proximity to the emulsion oil water interface which is the point most susceptible to oxidation damage. The specifically preferred CoQ10 is a reduced CoQ10 (i.e., ubiquinol) modified to have solubility in the water phase. The amount of CoQ10 within the oil phase can range from 0.25% to 5% of the oil on a w/w basis. The preferred amount of CoQ10 is within the range of 0.25% to 1.25%. The more preferred amount of the CoQ10 is within the range of 0.25% to 1.0%. The presence of CoQ10 in essentially any amount, including trace amounts, yields superior antioxidative stability of the lipid phase. The further ability of to regenerate oxidized forms of Vitamin E and glutathione by CoQ10 is a further synergistic benefit of the combination of glutathione and CoQ10.

The resulting testing has both expanded the range of acceptable pH modifiers (and the range of suitable pH from 2.8 to 6.6) and in fact has lead to the more preferred pH modifiers now including gallic acid, fumaric acid, pantothenic acid, and choline citrate. The combination of the preferred pH modifiers have a synergistic effect in terms of oxidative stability with the further inclusion of electron transfer mediators. The role of said electron transfer mediators has been further elucidated as a superior understanding of the theory explaining the significant gains in antioxidative stability being largely attributed to the creation of an electron transfer bridge at the interface of the oil and water phases of emulsions in general and particularly in the more susceptible nanoemulsions.

Additional more preferred polyols now include trehalose. The combination of trehalose with the noted electron transfer mediators yield superior oxidative stability. Trehalose has the secondary advantage of protecting the protein and/or protein fragment, an important benefit in providing enhanced antioxidative stability when the protein is exposed to elevated temperatures and/or when the emulsion is dried. The addition of such protein stabilizers include polyethylene glycol "PEG" also provides surface modification of the protein and/or protein fragment. Thus the utilization, without being bound by theory, of trehalose and/or PEG provides further encapsulation of the lipid phase within the micelles.

Additional more preferred phospholipids includes phospholipids rich in phosphatidylcholine "PC" and phospholipids rich in phosphatidylserine "PS". Rich is contextually defined as being of greater than 40% on a weight basis. PS rich phospholipids serves the role of binding the iron contained from the egg yolk phospholipids when the pH is circa 6.0. Thus the preferred formulation is the inclusion of PS rich phospholipids into the oil phase post emulsification. The utilization of PC rich phospholipids is important in an integral component on the interaction of a polycationic milk peptide complex with negatively charged bilayers, such as PC rich phospholipids. The combination markedly reduces the fluid spacing between the negatively charged lipid bilayers. These bridges are stabilized by increased adhesion arising from increased van der Waals interactions between the opposing bilayers, electrostatic intereactions between the pi electrons in the phenol ring (e.g., tocopherols) and the —(N.sup.+.CH.sub.3). sub.3 groups on the PC headgroups, decreased hydration repulsion between bilayers, and hydrogen bonds between the H-bond-donating moieties on the polyphenols, particulary tocopherols, and H-bond-accepting groups n the bilayer. The increased bilayer adhesion is essential for enhanced oxidative stability of emulsions.

One exemplary formulation procedure is the homogenization of Omega Pure menhaden fish oil (25%) for 4 minutes with egg yolk phospholipids "rich" in PC at 0.2% w/w (Sigma Chemical 60% PC) based on the weight of the fish oil, then 0.25% gamma cyclodextrin encapsulated CoQ10 (w/w, based on the weight of the fish oil) is added with subsequent homogenization for 4 minutes. An aqueous solution (75% of double deionized water) containing mannitol (4% w/w/, based on the weight of the emulsion) and trehalose (2% w/w, based on the weight of the emulsion) is magnetically stirred for 4 minutes. Gallic acid (0.2% w/w, based on the weight of the emulsion) is subsequently added and magnetically stirred for 2 minutes. The pH of this aqueous solution (water phase) is adjusted to pH 6.0 with the preferred electron transfer mediator of potassium hydroxide 0.1 N (alternatively/preferably a combination of KOH and choline citrate is used). The earlier prepared caprine casein phosphopeptide-chitosan complex (0.04% w/w, based on the weight of the emulsion) is added to this aqueous solution and homogenized for 1 minute. The oil phase and aqueous phase are combined and homogenized for 4 minutes (production methods would include multiple pass high pressure homogenization) resulting into an oil in water emulsion. The resulting oil in water emulsion is optionally contains subsequently added phospholipids rich in PS (Chemi Nutra-SerinAid TM). Without being bound by theory, the resulting micelles at the interface between the oil and water phase contain an iron-sulfur cluster as a means to provide an electron transfer bridge across the two phases.

Additional more preferred casein phosphopeptides are complexed with additional minerals including, though not limited to, magnesium, manganese, selenium, zinc, and iron. The particularly preferred mineral is in the lactate form. And the specifically preferred mineral is zinc lactate. Zinc has secondary advantages associated with protection of RNA and DNA, while calcium has secondary advantages associated with the many health benefits as known in the art for calcium including bone building, and cholesterol reduction.

Without being bound by theory, the creation of iron sulfur clusters is a fundamental component in the electron transfer from the oil phase into the water phase of the emulsion. Thus, effectively an electron transfer bridge is created across the interface of between the oil and water phase. The existence of this electron transport bridge is critical to the realization of significantly superior oxidative stability of lipids. The irony of this result is such that, iron which is otherwise a procatalyst, must be present in at least trace amounts as a means of creating the electron transfer bridge. Such electron transport bridge includes thialoto-bridged complexes. Electron-rich thiolato groups have a great affinity for various metal ions. This includes metal-bound thiolato sulfur centers. Broadly, the incorporation of thiolated complexes, metalloproteins and/or protein complex having an iron-sulfur cluster within the emulsion interface, without being bound by theory, enhances electron transfer between the phases.

Additional preferred proteins include keratin and canola, and fragments thereof of keratin and canola protein isolates. More preferred proteins include phophopeptides of keratin and canola proteins. A supplier of keratin includes Keratec of New Zealand with the preferred product being their Keratec IFP™, a purified protein fraction isolated from pure New Zealand wool. The Keratec Pep product has a high proportion of cystine derived amino acids as part of the peptide backbone. The particularly preferred Keratec product is Cynatine FLX™. A supplier of canola protein isolates includes Burcon of Canada in the form of Puratein™ and Supertein™.

Additional emulsifiers include the utilization of non-ionic emulsifiers such that the polycationic charge created by the chitosan is not "bound" by the emulsifier.

Additional antioxidants include vanillin, bee propolis, grape seed extract, grape pomace extract, quercitin, carotenoids, and lactoferrin. A preferred antioxidant has reducing sugars eliminated from the antioxidant. Numerous methods exist as known in the art, including the enzymatic elimination of sugars such as glucoseoxidase. Lactoferrin, a recognized powerful antioxidant, provides a synergistic impact of binding otherwise pro-oxidant iron, thus without being bound by theory effectively removes the catalytic iron while providing the inherent antioxidant benefits.

The further inclusion of an electron transfer mediator within the antioxidant and nanoemulsion compositions, without being bound by theory, enhances electron transfer out of the lipid phase of the emulsion into the water phase. The preferred electron transfer mediator is potassium hydroxide, an acceptable food ingredient. The potassium hydroxide serves a significant secondary role of providing potassium mineral supplementation, a noted deficient mineral especially in the American diet.

Without being bound by theory, the inventive combination of an electron transfer mediator, a molecular electron transfer bridge, and an iron-sulfur cluster (or metalloproteins) creates an aqueous, room temperature electride solution as indicated by the presence of a sapphire blue solution indicative of free electrons. A wide range of applications are anticipated for stable room temperature electride solutions, including nutraceutical, pharmaceutical, energy transfer, and oxidative stability applications.

Although only exemplary embodiments of the invention are specifically described above, it will be appreciated that modifications and variations of these examples are possible without departing from the spirit and intended scope of the invention.

What is claimed is:

1. A nanoemulsion composition comprising a protein or protein fragment complex having an electron transfer bridge between the oil and water interfaces of the nanoemulsion, wherein the nanoemulsion is selected from the group consisting of water-in-oil nanoemulsion and oil-in-water nanoemulsion, wherein the electron transfer bridge is selected from the group consisting of an iron-sulfur cluster, an electride solution, metalloproteins, or a metal-bound thiolato sulfur center, and at least one phospholipid selected from the group consisting of: phospholipids having greater than 40% phosphatidylcholine and phospholipids having greater than 40% phosphatidylserine, egg yolk phospholipids, soybean phospholipids, and combinations thereof.

2. The composition of claim 1, further comprising at least one of sulfated polysaccharides, electron transfer mediator, metalloproteins, and protein stabilizers.

3. The composition of claim 2, further comprising the sulfated polysaccharide selected from the group consisting of iota-carrageenan, kappa-carrageenan, lambda-carrageenan, chondroitin, heparin, dextran, and cyclodextrins, and combinations thereof.

4. The composition of claim 2, wherein the protein stabilizer is selected from the group consisting of trehalose and polyethylene glycol.

5. The composition of claim 1, wherein the complex is selected from the group of protein or protein fragments consisting of casein, casein fragment, canola protein isolate, canola protein fragment, keratin protein isolate, and keratin protein fragment.

6. The composition of claim 1, further comprising a medium-chain triglyceride.

7. The composition of claim 6, further comprising a medium-chain triglyceride selected from the group consisting of: caproic (C:6.0), caprylic (C:8.0), and capric (C:10.0) triglycerides, and any combinations thereof.

8. The composition of claim 1, further comprising at least one non-reducing sugar or sugar polyol.

9. The composition of claim 1, wherein the electron transfer bridge further comprises a casein fragment selected from the group consisting of: alpha-casein, beta-casein, kappa-casein, fragments thereof, and any combinations thereof.

10. The composition of claim 1, wherein the electron bridge further comprises a casein fragment comprises a caprine casein or fragment thereof.

11. The composition of claim 1, further comprising at least one phosphopeptide, glycopeptide, glyceride and combinations thereof.

12. The composition of claim 11, further comprising a phosphopeptide having amounts of $alpha_{s2}$-casein greater than 15 percent of total casein and medium-chain triglycerides.

13. The composition of claim 12, further comprising a caseinophosphopeptide.

14. The composition of claim 13, wherein the caseinophosphopeptide comprises a caprine caseinophosphopeptide.

15. The composition of claim 11, wherein the glyceride is selected from the group consisting of: enzymatically modified oils, fats, and fatty acids of mono-, di-, and tri-glycerides; lipolyzed modified oils, fats, and fatty acids of mono-, di-, and tri-glycerides; and combinations thereof.

16. The composition of claim 1, further comprising at least one ingredient selected from the group consisting of: alpha, beta, gamma or delta tocopherols, alpha, beta, gamma or delta tocotrienols, tocopherols, tocotrienols, beta-carotene, phospholipids, chitosan, Coenzyme $Q_{10}$, glutathione, ubiquinol, reduced Coenzyme $Q_{10}$, reduced glutathione, vanillin, quercetin, lactoferrin, carotenoids, and combinations thereof.

17. The composition of claim 1, further comprising at least one ingredient selected from the group consisting of delta-5 desaturase enzyme suppression actives, sesame lignans, L-carnitine components, permeation enhancers, oils rich in Omega-3, pH modifiers, chelating agents, polyphenols, modified starches, glycerides, fruit concentrate sweeteners, cocoa powder, Sucralose, and oil-soluble flavors, vitamins, nutraceutical actives, and pharmaceutical actives.

18. The composition of claim 17, wherein the pH modifier comprises pH modifiers selected from the group consisting of: choline citrate, alpha lipoic acid, gallic acid, fumaric acid, pantothenic acid, citric acid, ascorbic acid, gluconic acid, and combinations thereof.

19. The composition of claim 17, wherein the chelating agent comprises citric acid.

20. The composition of claim 17, wherein the polyphenols are selected from the group consisting of polyphenols derived from the fruit of Solanum melongena, polyphenols derived grapes including grape seed extract and grape pomace extract, enzymatically modified polyphenols as a means of eliminating reducing sugars including bee propolis, or combinations thereof.

21. The composition of claim 17, wherein the fruit concentrate sweetener comprises: a blend of hydrolyzed starch having a dextrose equivalent (D.E.) of up to approximately 25; fruit juice or fruit syrup concentrate of at least approximately 40% soluble solids; and approximately 0% insoluble solids, wherein the starch, juice or concentrate and solids form a liquor having a dry weight composition of approximately 40 to approximately 65% complex carbohydrates, approximately 35 to approximately 55% simple sugars from the fruit juice or fruit syrup concentrate, and approximately 0 to approximately 5% nutritional components occurring naturally in the fruit juice or fruit syrup concentrate.

22. The composition of claim 1, wherein the nanoemulsion thereof further comprises chitosan, thiolated chitosan, and chitosan-alpha lipoic acid complex as a means to enhance bioadhesion.

23. The composition of claim 1, wherein the nanoemulsion further comprises delta-5 desaturase enzyme suppression actives.

24. The composition of claim 1, wherein the nanoemulsion further comprises sesame lignans.

25. The composition of claim 1, wherein the nanoemulsion further comprises L-carnitine components.

26. The composition of claim 1, wherein the nanoemulsion further comprises a calcium, magnesium, zinc, manganese, selenium, potassium, or iron salt or combination thereof; and an oil rich in Omega-3 products.

27. The composition of claim 1, wherein the nanoemulsion further comprises an edible oil selected from the group consisting of vegetable oil and microalgae oils.

28. The composition of claim 1, wherein the nanoemulsion further comprises a vegetable oil rich in Omega 3 or conjugated linoleic acid.

29. The composition of claim 1, wherein the nanoemulsion further comprises a vegetable oil selected from the group consisting of rice bran oil, flaxseed oil, chia oil, hemp oil, castor oil, soybean oil, lesquerella oil, dehydrated castor oil, oils rich in Omega-3 or conjugated linoleic acid.

30. The composition of claim 1, wherein the nanoemulsion further comprises an animal oil rich in Omega 3 and is selected from the group consisting of fish oil or egg oil.

31. The composition of claim 1, wherein the nanoemulsion further comprises a calcium, magnesium, zinc, manganese, selenium, potassium, or iron salt or combination thereof, and the nanoemulsion is present in a transparent beverage product.

32. The composition of claim 1, wherein the nanoemulsion further comprises an enzymatically modified protein and the enzymatic modification is by trypsin digestion, and the protein is caprine casein characterized by a content of $alpha_{s2}$-casein greater than 15 percent and beta-casein greater than 15 percent of the total casein.

* * * * *